(12) United States Patent
Zhang et al.

(10) Patent No.: US 6,955,819 B2
(45) Date of Patent: Oct. 18, 2005

(54) METHODS AND APPARATUS FOR USING CONTROLLED HEAT TO REGULATE TRANSDERMAL AND CONTROLLED RELEASE DELIVERY OF FENTANYL, OTHER ANALGESICS, AND OTHER MEDICAL SUBSTANCES

(75) Inventors: Jie Zhang, Salt Lake City, UT (US); Wade Hull, Taylorsville, UT (US); Larry Rigby, Salt Lake City, UT (US); Theodore Stanley, Salt Lake City, UT (US)

(73) Assignee: Zars, Inc., Salt Lake City, UT (US)

( * ) Notice: Subject to any disclaimer, the term of this patent is extended or adjusted under 35 U.S.C. 154(b) by 513 days.

(21) Appl. No.: 09/796,250

(22) Filed: Feb. 28, 2001

(65) Prior Publication Data

US 2001/0037104 A1 Nov. 1, 2001

Related U.S. Application Data

(60) Continuation-in-part of application No. 09/545,591, filed on Apr. 7, 2000, which is a division of application No. 09/162,890, filed on Sep. 29, 1998, now Pat. No. 6,245,347.
(60) Provisional application No. 60/185,913, filed on Feb. 29, 2000.

(51) Int. Cl.[7] .............................. A61K 9/70; A61F 13/00
(52) U.S. Cl. ...................... 424/449; 424/401; 424/443; 424/447
(58) Field of Search ................................ 424/401, 443, 424/449

(56) References Cited

U.S. PATENT DOCUMENTS

| | | | |
|---|---|---|---|
| 3,929,131 A | 12/1975 | Hardwick | 128/254 |
| 4,210,670 A | 7/1980 | Cooke | 424/324 |
| 4,230,105 A | 10/1980 | Harwood | 128/156 |
| 4,286,592 A | 9/1981 | Chandrasekaran | 128/260 |

(Continued)

FOREIGN PATENT DOCUMENTS

| | | |
|---|---|---|
| GB | 2 163 956 A | 12/1988 |
| WO | 88/09169 | 1/1988 |
| WO | WO 97/01310 | 1/1997 |
| WO | WO 97/01311 | 1/1997 |
| WO | WO 97/01312 | 1/1997 |
| WO | WO 97/01313 | 1/1997 |
| WO | WO 97/36968 | 10/1997 |
| WO | WO 97/49361 | 12/1997 |
| WO | WO 98/28021 | 7/1998 |
| WO | WO 98/28024 | 7/1998 |
| WO | WO 98/29063 | 7/1998 |
| WO | WO 98/29064 | 7/1998 |
| WO | WO 98/29065 | 7/1998 |
| WO | WO 98/29066 | 7/1998 |
| WO | WO 98/29067 | 7/1998 |
| WO | WO 99/09917 | 3/1999 |
| WO | WO 99/09918 | 3/1999 |

OTHER PUBLICATIONS

Arky, et al., *Physicians' Desk Reference*, 1997, pp. 1336–1340.

Mack Publishing Company, "Stability of Phamaceutical Products," *Pharmaceutical Sciences*, pp. 1481–2, 1985.

(Continued)

*Primary Examiner*—Shelley A. Dodson
*Assistant Examiner*—Konata M. George
(74) *Attorney, Agent, or Firm*—Kirton & McConkie; Michael F. Krieger (57) ABSTRACT

The present invention is directed toward an apparatus to rapidly deliver a drug to a patient The invention comprises a drug beneath a patient's skin in a drug depot site. A heating component is placed near the drug depot site and generates heat in and near the drug depot site. A control component connected to the heating component is used to control the magnitude and duration of heat generated by the heating component.

37 Claims, 6 Drawing Sheets

U.S. PATENT DOCUMENTS

| | | | |
|---|---|---|---|
| 4,529,601 A | 7/1985 | Broberg et al. | 514/626 |
| 4,685,911 A | 8/1987 | Konno et al. | 604/897 |
| 4,693,706 A | 9/1987 | Ennis, III | 604/87 |
| 4,747,841 A | 5/1988 | Kuratomi et al. | 604/291 |
| 4,830,855 A | 5/1989 | Stewart | 424/448 |
| 4,898,592 A | 2/1990 | Latzke et al. | 604/307 |
| 4,911,707 A | 3/1990 | Heiber et al. | 424/449 |
| 4,913,957 A | 4/1990 | Strack et al. | 424/286 |
| 4,963,360 A | 10/1990 | Argaud | 424/443 |
| 4,994,049 A | 2/1991 | Latzke et al. | 604/307 |
| 5,108,710 A | 4/1992 | Little et al. | 422/104 |
| 5,114,411 A | 5/1992 | Haber et al. | 604/203 |
| 5,128,137 A | 7/1992 | Muller et al. | 424/449 |
| 5,147,339 A | 9/1992 | Sundström | 604/307 |
| 5,213,129 A | 5/1993 | Someah et al. | 137/101.11 |
| 5,217,718 A | 6/1993 | Colley et al. | 424/449 |
| 5,229,133 A | 7/1993 | Wright et al. | 424/473 |
| 5,276,032 A | 1/1994 | King et al. | 514/239 |
| 5,279,594 A | 1/1994 | Jackson | 604/265 |
| 5,329,976 A | 7/1994 | Haber et al. | 141/25 |
| 5,330,452 A | 7/1994 | Zook | 604/307 |
| 5,364,350 A | 11/1994 | Dittman | 604/89 |
| 5,534,021 A | 7/1996 | Dvoretzky et al. | 607/112 |
| 5,580,573 A | 12/1996 | Kydonieus et al. | 424/449 |
| 5,605,536 A | 2/1997 | Sibalis | 604/20 |
| 5,626,571 A | 5/1997 | Young et al. | 604/370 |
| 5,651,768 A | 7/1997 | Sibalis | 604/20 |
| 5,658,583 A | 8/1997 | Zhang et al. | 424/402 |
| 5,662,624 A * | 9/1997 | Sundstrom et al. | 604/291 |
| 5,728,057 A | 3/1998 | Ouellette et al. | 602/62 |
| 5,728,058 A | 3/1998 | Ouellette et al. | 602/62 |
| 5,728,146 A | 3/1998 | Burkett et al. | 607/109 |
| 5,733,255 A | 3/1998 | Dinh et al. | 604/20 |
| 5,735,889 A | 4/1998 | Burkett et al. | 607/96 |
| 5,741,318 A | 4/1998 | Ouellette et al. | 607/108 |
| 5,837,005 A | 11/1998 | Viltro et al. | 607/112 |
| D403,778 S | 1/1999 | Davis et al. | D24/206 |
| D403,779 S | 1/1999 | Davis et al. | D24/206 |
| 5,860,945 A | 1/1999 | Cramer et al. | 602/62 |
| D407,822 S | 4/1999 | Davis et al. | D24/206 |
| D407,824 S | 4/1999 | Davis et al. | D24/206 |
| D408,923 S | 4/1999 | Davis et al. | D24/206 |
| D409,757 S | 5/1999 | Davis et al. | D24/206 |
| 5,904,710 A | 5/1999 | Davis et al. | 607/108 |
| 5,906,637 A | 5/1999 | Davis et al. | 607/108 |
| 5,906,830 A | 5/1999 | Farinas et al. | 424/448 |
| 5,918,590 A | 7/1999 | Burkett et al. | 126/263.02 |
| 5,919,479 A | 7/1999 | Zhang et al. | 424/449 |
| 5,925,072 A | 7/1999 | Cramer et al. | 607/108 |
| D412,751 S | 8/1999 | Davis et al. | D24/206 |
| D417,283 S | 11/1999 | Davis et al. | D24/206 |
| 5,980,562 A | 11/1999 | Ouellette et al. | 607/108 |
| 5,984,995 A | 11/1999 | White | 75/230 |
| D418,606 S | 1/2000 | Davis et al. | D24/206 |
| 6,019,782 A | 2/2000 | Davis et al. | 607/96 |
| 6,020,040 A | 2/2000 | Cramer et al. | 428/64.1 |
| 6,024,761 A | 2/2000 | Barone et al. | 607/108 |
| 6,042,673 A | 3/2000 | Johnson et al. | 156/227 |
| 6,048,326 A | 4/2000 | Davis et al. | 602/26 |

OTHER PUBLICATIONS

McCafferty, et al.,"Comparative In Vivo and In Vitro Assessment of the Percutaneous Absorption of Local Anaesthetics," *British Journal of Anaesthesia*, vol. 60, (1988), 64–69.

Woolfson, et al., "Concentration Response Analysis of Percutaneous Local Anaesthetic Formulations," *British Journal of Anaesthesia*, vol. 61, (1988), pp. 589–592.

McCafferty, et al., "In Vivo Assessment of Percutaneous Local Anaesthetic Preparations," *British Journal of Anaesthesia*, vol. 62, (1989), pp. 17–21.

Knutson et al., "Solvent–Mediated Alterations of the Stratum Corneum," *Journal of Controlled Release*, vol. 11, (1990), pp. 93–103.

Lycka, "EMLA, A New and Effective Topical Anesthetic," *J. Dermotol., Surg. Oncol.*, vol. 18, (1992), pp. 859–862.

McCafferty, et al., "New Patch Delivery System for Percutaneous Local Anaesthesia," *British Journal of Anaesthesia*, vol. 71, (1993) pp. 370–374.

Woolfson, *Percutaneous Local Anaesthesia*, E. Horwood, N.Y. (1993), pp. 166–170.

"Room Temperature," Macmillan, U.S.A., *Webster's New World College Dictionary*, Third Edition, 1997, p. 1165.

Florey, Klaus, *Analytical Profiles of Drug Substances*, vol. 15, 1986, pp. 150–231.

Florey, Klaus, *Analytical Profiles of Drug Substances*, vol. 12, 1983, pp. 73–105.

"Local Anesthetics, Parenteral, General Statement," *AHFS Drug Information*, 1992.

Florey, Klaus, *Analytical Profiles of Drug Substances*, vol. 18, 1989, pp. 379–411.

Sakamoto et al., "Dermal patch anesthesia: comparison of 10% lignocaine gel with absorption promoter and EMLA cream," *Anesthesia*, (1993), vol. 48, pp. 390–392.

Dvoretzky, Israel, M.D., Hyperthermia Therapy for Warts Utilizing a Self–adminstered Exothemic Patch, *Dermal Surgery*, (1996), vol. 22, pp. 1035–1039.

Stern, Peter, M.D. and Levine, Norman, M.D., "Controlled Localized Heat Therpay in Cutaneous Warts," *Arch Dermatol*, (Jul. 1992), vol. 128, pp. 945–948.

* cited by examiner

Heating Patch #1

Heating Patch #2

Heating Patch #3

Heating Patch #4

Heating Patch #5
(same as Heating patch #1)

Drug patch

A combination of heating disc and an accommodating pouch at the back of he fentanyl dermal patch that only allows one way to insert the heating disc into the pouch.

FIG. 5

METHODS AND APPARATUS FOR USING CONTROLLED HEAT TO REGULATE TRANSDERMAL AND CONTROLLED RELEASE DELIVERY OF FENTANYL, OTHER ANALGESICS, AND OTHER MEDICAL SUBSTANCES

RELATED APPLICATION

This application is a continuation-in-part of U.S. patent application Ser. No. 09/545,591 filed Apr. 7, 2000; which is a divisional of U.S. patent application Ser. No. 09/162,890 filed Sep. 29, 1998 now U.S. Pat. No. 6,245,347. This application also claims priority to U.S. Provisional Application No. 60/185,913 filed Feb. 29, 2000.

BACKGROUND

1. The Field of the Invention

The present invention is more specifically directed toward an apparatus and method for selectively heating and releasing medical substances from transdermal delivery systems and depot sites in or under a patient's skin or from injected or implanted controlled release systems.

2. The Background Art

Transdermal drug delivery affords users and patients distinct advantages over other delivery methods and techniques. Patients prefer transdermal administration in some cases because of the ease of administration and because transdermal drugs are delivered noninvasively. Care givers also appreciate the ease of administration and the ability to deliver a drug over a long period of time. Transdermal delivery in many cases avoids first pass elimination of drugs. Because of these advantages, transdermal drug delivery has grown in popularity and interest in studying transdermal drug delivery has increased.

Transdermal drug delivery occurs as a drug formulation is brought into contact with a patient's skin. In transdermal drug delivery, it often occurs that some of the drug gets stored in skin and sub-skin tissues after penetrating the skin. This effect is referred as "depot effect", and the storage site as "depot" or "depot site" hereafter. As blood circulates through these tissues, the drug is absorbed into the blood stream and delivered throughout the systemic circulation. It is discovered that by placing heat on or near an administration site of a transdermally delivered drug, the heat will not only increase the skin's permeability, but also greatly increase the circulation in the tissues and have other effects that allow the drug to be absorbed more quickly into the systemic circulation. It has been suggested by the inventor that heat be used to increase onset time and to increase the amount of drug being absorbed into the skin.

Nothing in the prior art has taught that transdermal drug delivery is capable of rapidly responding to changing needs in a patient. The time it takes for the drug to be delivered from the drug formulation to the skin, be absorbed into the skin and surrounding tissues and from there absorbed into the systemic circulation and delivered throughout the systemic circulation has been seen as a barrier for rapid response or modification of the drug circulation in systemic circulation. Given this perception of transdermal drug delivery, techniques such as patient controlled analgesia (PCA) have not been attempted using transdermal drugs. Patient controlled analgesia may require the ability of the patient to choose when a particular dose will be delivered, the ability of the care giver to set or prescribe the amount that will be delivered rapidly on demand, and the ability to prevent or lock-out the patient from excessively self-dosing.

In addition to the perceived physiological barriers to rapidly delivering drugs transdermally, the technology used in conjunction with transdermal drug delivery as taught in the prior art is not capable of sophisticated delivery techniques such as PCA. Current PCA treatment requires both sophisticated medical instruments and trained personnel. Current technologies are invasive, require carefully calibrated pumps and other equipment, all of which can be expensive. It would be advantageous therefore to develop a transdermal drug delivery system, which can rapidly respond to a patient's changing needs, that could deliver an additional drug dose quickly (referred to as bolus drug hereafter), and that could allow a patient to control the delivery of the additional drug on demand that can allow the caregiver to prescribe how much extra drug the patient can obtain from self dosing, and that could allow the caregiver to set "lock-out" times to prevent the patient from excessively self-dosing. (Lock-out time is the time period in which no extra drug is delivered even if the patient triggers the self-dosing mechanisms.)

The present invention also provides for extended duration of drug delivery limited only by the supply of drug and availability of electric current. The present invention also provides the ability to vary intervals at which extra drug is delivered and the length of time by which the drug is delivered. The present invention also provides the ability to let the caregiver to set "lock-out" time. This can be accomplished through use of a microprocessor in conjunction with the electric healing component. The present invention provides the ability to respond quickly to the patient's need and provide the patient a drug dose on demand in a safe and effective manner. By using the present invention as described in the methods herein, a patient can self-administer analgesia (PCA) or other drugs where appropriate. The present invention allows the user a greater variety of methods of use and provides additional reliability such as more precise control over the areas, either the temperatures at which they are heated and the duration for which they are heated. The present invention provides a variety of temperature profiles. The present invention does not require the continued replacement of the heating element.

It should be pointed out that the methods and apparatus presented in this invention may provide extra drug from controlled release formulations or devices implanted or injected into the skin or sub-skin tissues. In other words, the user may create a "depot site" by implanting or injecting drug into the skin and sub-skin tissues.

BRIEF SUMMARY AND OBJECTS OF THE INVENTION

Using the present invention, an extra bolus of drug can be delivered into the patient's body by heating the skin and sub-skin tissues under a transdermal drug delivery system that has been on the skin for sufficient time to establish a depot site (or "depot") of the drug in said tissues. A depot is formed when part of the drug delivered across the skin gets absorbed into the skin and/or sub-skin tissues, such as fatty tissues, and gets stored there. Using the present invention, heat is used to rapidly drive drug from the depot into the systemic circulation by mechanisms such as increased blood flow.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

Prior to the present invention, those skilled in the art understood transdermal drug delivery to be a slow process, with slow onset, slow offset, and relatively smooth delivery rates. However, recent experiments with transdermal fentanyl patches using the present invention revealed that blood drug concentrations can rise rapidly and significantly following heating. These preliminary results revealed that serum fentanyl concentrations increased very rapidly (within 5–10 min) and significantly (>50%) following the commencement of the heating and stayed elevated for an extended period of time. Therefore, a serum fentanyl concentration increase (more than 50% within 5–10 min.) using the present invention is very surprising. These results indicate that releasing a significant portion of fentanyl stored in the depot into the systemic circulation by heating can be a rapid process, and can be achieved with relatively brief heating.

The results of recent studies show dramatic improvements in drug delivery using oxidation heating the drug in the sub-skin depot. The present invention employs the principle of heating the drug in the sub-skin depot in a precisely regulated PCA environment. The present invention provides new methods and apparatus to rapidly deliver extra drug to the patient to accommodate his/her changing needs. For some drugs, a relatively short heating period is all that is required to significantly increase serum drug concentrations. To facilitate the delivery of such drugs using the present invention, a compact battery-powered heating source/control apparatus with various important and useful features is provided. A highly accurate, reliable, and precise control apparatus may be necessary to safely and effectively deliver the bolus drug from sub-skin tissues by heating, since the drug release from depot can be very sensitive to the temperature increase. The temperature control of the heating as well as heating area must be very precise in order to accurately deliver the desired amount of bolus drugs. For example, it is believed that an increase of 15–20 percent in serum fentanyl levels is sufficient to treat a typical episode of breakthrough cancer pain. A much higher increase may not only be unnecessary, but may also be dangerous. The present invention provides novel methods and apparatus for using heating to deliver bolus drugs from sub-skin depot sites in a highly precise, controllable, and convenient way.

Methods and apparatus for using exothermic chemical reaction for manipulating transdermal drug delivery have been described in detail in issued patents and pending patent applications. Methods and apparatus for using electrically heated device for similar purposes were also described. However, these heating methods may not be suited for promoting beneficially handling responsive heating-induced serum fentanyl concentration increases of the present invention. Moreover, the present invention contemplates and dramatically increases the feasibility of using sophisticated electronically controlled heating device to achieve rapid, selective, and well-controlled delivery of extra drug.

The present invention comprises three essential parts: a drug depot site (which may be produced by transdermal delivery or injection or implantation), a heating component to generate heat for heating the drug depot site and/or surrounding tissues, and a control component that controls the heating temperature on the depot site. The heating component is preferably an electric heating component. The electric heating component and control component are connected by electric wires. The method of the present invention comprises the steps of creating a depot site beneath a patient's skin and selectively applying controlled heat to the depot site to release a portion of the drug from the depot site to the systemic circulation.

The present invention also relates to methods and apparatus for using the heating component and the control component to heat the skin under a drug patch in the initial phase of the patch application to increase skin permeability in order to significantly shorten the onset time of the drug patch. Since there is little depot in the initial phase of the patch application, the main effect of the heating is increasing skin permeability, rather than release drug from depot.

In a preferred embodiment, the control component may have a mechanism that allows the patient to trigger the delivery of a pre-determined amount of bolus drug from the depot and the drug patch. For example, when a button on the control component (e.g. a PCA button) is pushed, the pre-programmed control component sends an electric current with pre-determined magnitude through wires to the heating component for a pre-determined length of time. The magnitude and the duration of the current are such that it produces a temperature increase at the skin for a duration that releases a pre-determined amount of the drug from the depot into the systemic circulation. The magnitude of the current may be designed to produce different heating temperature vs. time profiles to accommodate different needs. For example, a gradual increase followed by steady state heating temperature may minimize the discomfort associated with the sudden increase in skin temperature. FIG. 1 shows some examples of the temperature vs. time profiles.

The control component may also have a mechanism to allow the physician or care giver to choose from several pre-programmed heating temperature profiles which correspond to different amounts of extra drug. For example, the physician may choose a profile that heats for five minutes at a predetermined temperature for treating a patient suffering from episodes of mild breakthrough pain, and a profile that heats for fifteen minutes at the same temperature for another patient who usually suffers from episodes of more severe breakthrough pain. Or, the physician may choose a profile that increases the temperature at the patch by 2° C. from the unheated temperature for ten minutes for the first patient and another profile with 4° C. by ten minutes for the latter patient.

A simpler version of the apparatus may have settings in the control component that correspond to pre-determined electric power and heating time combinations. Each setting delivers a different pre-determined amount of heating energy (in the form of different heating temperature and duration) to the skin site. With this simpler version of the apparatus, the temperature of the skin is not monitored. But the electric power in each setting is pre-determined to be safe to the skin. This simpler version does not have the temperature sensor, monitoring, and feedback system, so the cost is lower. This may increase the feasibility of a disposable heating component.

The control component also may have the mechanism to allow the physician to set "lockout" times, which is the length of time in which the device generates no heat even if the patient tries to trigger the delivery of extra drug. The "lockout" feature is commonly used in PCA devices for preventing drug overdose. It may also serve the purpose of allowing sufficient time to re-fill the depleted depot in the tissues under the drug patch.

The control component may have a mechanism that receives a temperature signal from a temperature sensor proximate to the skin or drug patch and adjusts the electric current to the heating component accordingly.

In a preferred embodiment, the heating component is capable of generating heat when supplied with electric current. It may also have a temperature sensor that can sense the temperature at the drug patch or skin and feed it back to the control component to regulate the heating temperature. The heating component may also have a layer of thermal insulating material on the side-not in contact with the drug patch for minimizing heat loss and maintaining a more stable temperature at the skin, even when there is no heating.

BRIEF DESCRIPTION OF THE DRAWINGS

The foregoing and other objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described and explained with additional specificity and detail through the use of the accompanying drawings in which:

DETAILED DESCRIPTION OF THE PREFERRED EMBODIMENTS

It will be readily understood that the components of the present invention, as generally described and illustrated in the figures herein, could be arranged and designed in a wide variety of different configurations. Thus, the following more detailed description of the embodiments of the system and method of the present invention, and represented in FIGS. 1 through 5, is not intended to limit the scope of the invention, as claimed, but is merely representative of the presently preferred embodiments of the invention.

The presently preferred embodiments of the invention will be best understood by reference to the drawings, wherein like parts are designated by like numerals throughout.

EXAMPLE 1

The surprising results of the controlled heat induced fentanyl bolus delivery were observed in a study of controlled heat-induced bolus delivery of fentanyl from a dermal fentanyl patch and drug depot in tissues under the patch.

The study had two parts (Arm #1, Arm #2). In the first part, a 25 mcg/hr Duragesic fentanyl dermal patch was applied on the chest skin of the human subject at t=0. At t=24 hrs, a heating patch capable of increasing the skin temperature to approximately 40–42 C for approximately 1 hr was placed on the Duragesic Patch. Both Duragesic and the heating patch were removed at t=30 hr. The heating patch had a heating area of about 40 $cm^2$. Blood samples were taken before t=0 and every hour on the hour thereafter for 36 hours. Additional blood samples were taken at 24 hr-5 min, 24 hr-10 min, 24 hr-15 min, 24 hr-20 min, 24 hr-30 min, 24 hr-40 min, 24 hr-50 min, and 25 hr-30 min. Serum samples were obtained from the blood samples via centrifugation. Concentrations of fentanyl in the serum samples were determined by a radioimmunoassay method.

In the second part of the study, the subject received similar treatment as in the first part, except that a heating patch capable of heating the skin temperature to approximately 40–42 C for approximately 4 hours were placed onto the Duragesic patch at t=0. The heating patch had a heating area of approximately 40 $cm^2$.

Serum fentanyl concentrations of the 5 subjects who completed both arms and that of another subject who completed only part are shown in Table I.

The results indicated that within 5–10 min of the commencement of heating after the Duragesic patch was on the skin for 24 hours, mean serum fentanyl concentrations of the subjects increased at least 60 percent.

The results also indicate that serum fentanyl levels reached steady state much sooner with the initial heating than without it.

The heating patches had a bottom wall (made of plastic tape, with the adhesive side facing away from the top wall), a top wall (made of plastic tape, with the adhesive side facing the bottom wall), and a heat-generating medium in a thin tissue bag. The edge of the top wall was adhered on the edge of the bottom wall to form a closed space between the walls. The tissue bag resided in the space. The top wall had pre-determined number of holes with predetermined size. The heat-generating medium comprised activated carbon, iron powder, fine wood powder, salt, and water. The heating patch was stored in an air-tight pouch immediately after manufacturing. Shortly before use, the heating patch was removed from the pouch. Oxygen in ambient air flows into the heat-generating medium via the hole in the top wall to cause heat-generating oxidation reaction. The heating temperature and duration are determined by the size and number of the holes in the top wall, as well as the quantity and composition of the heat-generating medium. For example, the heating patch that lasted approximated 4 hours had more heat-generating medium than the one that lasted about 1 hour.

It is generally known among the skilled in the art that transdermal drug delivery is a slow process, with slow onset, slow offset, and relatively smooth delivery rates. Therefore, a serum fentanyl concentration increase of 60 percent or more within 5–10 min is very surprising. These results suggest that a significant portion of fentanyl stored in the depot can be rapidly delivered to the systemic circulation by heating the depot site. This suggests that precise amount of bolus drug may be delivered into the systemic circulation by a short but precise heating of the patch and sub-patch tissues.

Surprisingly, the study shows that the heat-induced serum fentanyl concentration increase is faster than intramuscular injection and trans oral mucosal delivery, which are popular methods for delivering extra analgesics. These surprising findings support the conclusion that blood drug concentrations in a patient wearing a transdermal drug delivery patch can be rapidly changed by heating. While no sophisticate electric heating component was used in this study, the results suggested that serum fentanyl concentration changes can respond rapidly to heating, which is necessary for PCA.

EXAMPLE 2

In another example, the subject received similar treatment as in the second part of Example 1, except that a heating patch capable of heating the skin temperature to approximately 40–42 C for approximately 4 hours were placed onto the Duragesic patch at t=0. The heating patch had a heating area of approximately half the heating area described in Example 1.

The results indicated that within 5–10 min of the commencement of heating after the Duragesic patch was on the skin for 24 hours, mean serum fentanyl concentrations of the subjects increased at least 30 percent, or approximately half the increase shown in Example 1.

EXAMPLE 3

The apparatus of the present invention has a heating component and a control component. The two components are connected by wires. Optionally, the two components are connected by a detachable connector.

The heating component comprises a substantially two dimensional resistor heating element that can generate heat when supplied with electricity. The size and shape of the heating element may vary. If the heating element is attached to a transdermal drug delivery patch, the area of the heating component may be smaller, the same, or larger than the area of the drug patch, depending on the need. For example, a larger-than-drug-patch heating component may be needed to also heat the tissues surrounding the drug patch if a maximum speed of releasing the drug from the depot is desired.

The heating component may have a temperature sensor in contact with the drug patch such that the temperature sensor can sense the temperature and feed it back to the control component via the wires to regulate the temperature by controlling the electric current or voltage output to the heating element.

The heating component may be attached to the drug patch using various means such as hook and loop attachments, adhesive and pouches. Means to detach from the drug patch without removing the drug patch from the skin may also be provided.

The heating component may have a layer of insulating material (i.e. foam tape) on the side of the heating element that is not in contact with the drug patch (optional). The insulating layer can minimize the temperature variation due to outside environment and minimize the electric power needed to achieve desired heating temperature.

The heating element may be disposable or reusable.

The control component provides a mechanism for delivering different heating temperatures/durations, which corresponds to different bolus drug amounts.

This mechanism can be in the form of a multi-position dial switch. Each position on the dial switch corresponds to a pre-programmed heating temperature-time profile having a predetermined heating temperature and duration. The heat can release a pre-determined amount of drug from the depot under the drug patch.

The control component also may optionally comprise a mechanism for regulating heating temperature based on the signal from the temperature sensor. The temperature sensor may take a skin temperature measurement and/or a patch temperature measurement before heating. The control component then delivers adequate electric current or voltage (as a function of time) to the heating element to produce the pre-programmed temperature increase vs. time profile. Some examples of heating temperature profiles are shown in FIG. 1.

The sensor may continue to measure the temperature in the process of heating and feed it back to the control component to assure that the actual temperature is in the pre-determined range.

It is understood that the amount of bolus release from the depot may be more related to the change in the skin temperature from unheated to heated temperatures and heating duration than the absolute skin temperature.

If this is proven experimentally, then the temperature feed back system may not be needed, and the positions in the dial switch only need to correspond to different predetermined amounts of heating energy (in the form of different predetermined magnitudes of electric current or voltage and/or durations of the electric current or voltage). Of course, the electric current or voltage represented by each dial switch position must be pre-determined to avoid over heating the skin. A temperature sensor may still be used in a mechanism that will automatically turn off the electric current or voltage if a dangerously high temperature is sensed by the temperature sensor. This may be an important safety feature.

The control component has a delivery button. When the button is pushed, the control component delivers one episode of electric current or voltage to the heating component according to the setting on the dial switch (mentioned above). The setting may be predetermined by or selected by the physician or health care giver. The heating component then heats the drug patch skin and/or depot site for a pre-determined period of time with a pre-determined temperature profile. Thus, a pre-determined amount of bolus drug is delivered after the delivery button is pushed.

The control component also has a lockout mechanism that allows the physician to select a period of time in which the control component delivers no electric current to the heating element even if the delivery button is pushed.

This may be in the form of a dial switch with several positions, such as 5, 10, 15, 20, 30, 45, 60 minutes. For example, if the dial switch is set at 10 minute, the apparatus will generate no electric current for a period of 10 minutes after the last bolus, even if the delivery bottom is pushed. This is necessary to minimize the overdose risk and give enough time for the drug depot in the tissues under the drug patch to re-fill after last bolus.

EXAMPLE 4

Figure 3:
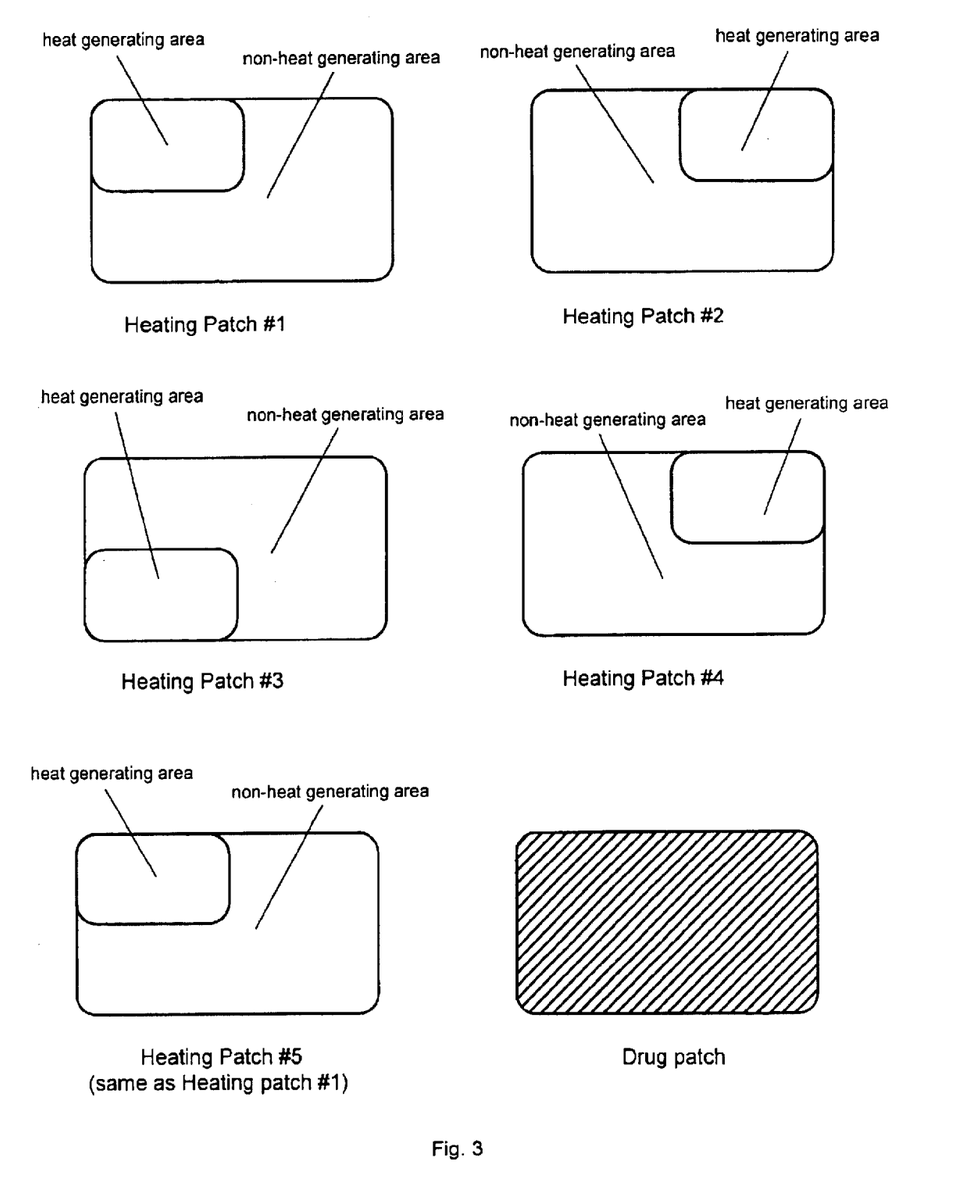
FIG. 3 is a heating component in the form of exothermic oxidation heating patch with a heating area covering a different fraction of the drug patch area.
Figure 4:
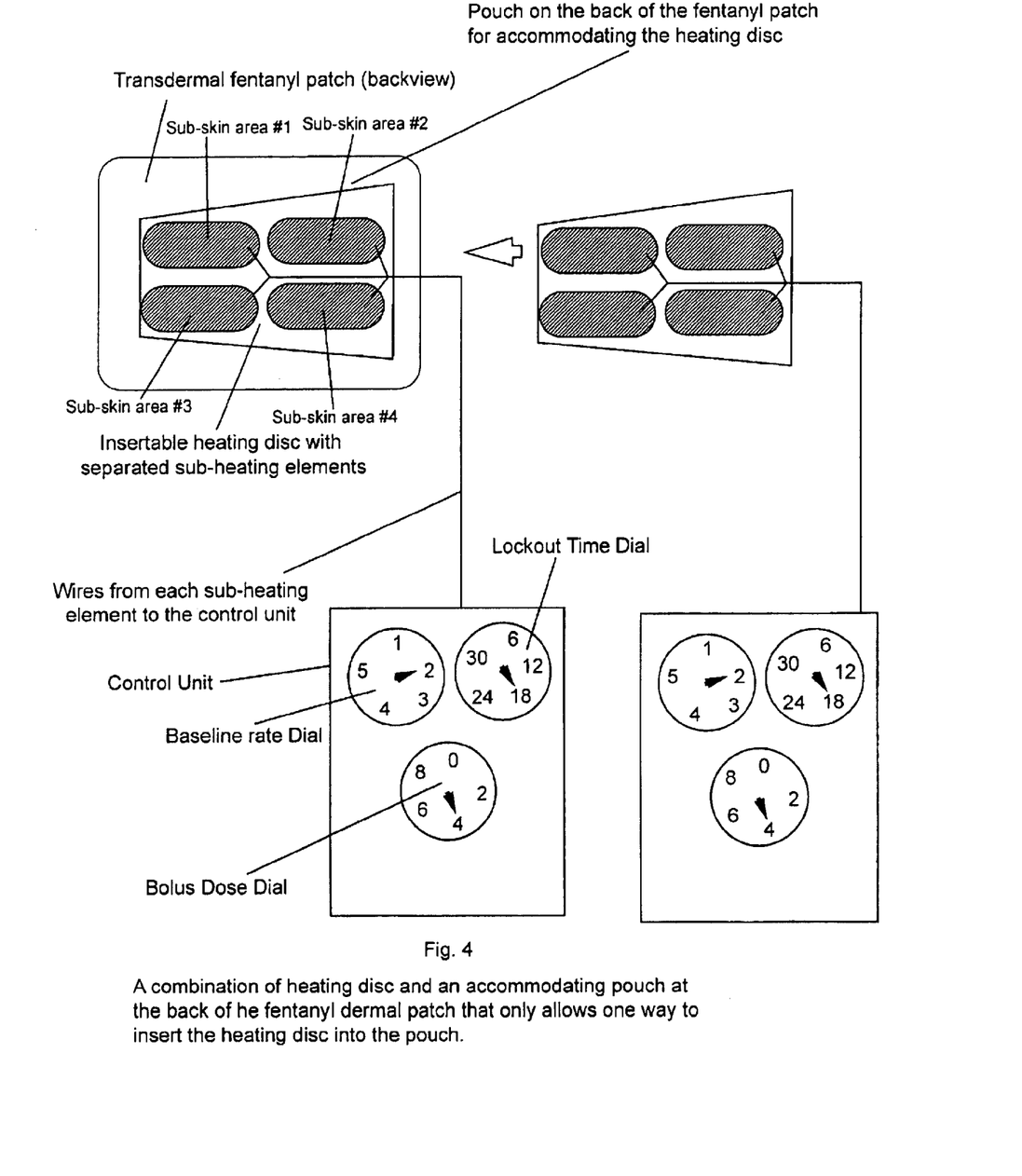
FIG. 4 shows a fentanyl patch sub-heating elements accommodating an electric heating apparatus with sub-heating elements.
Figure 5:
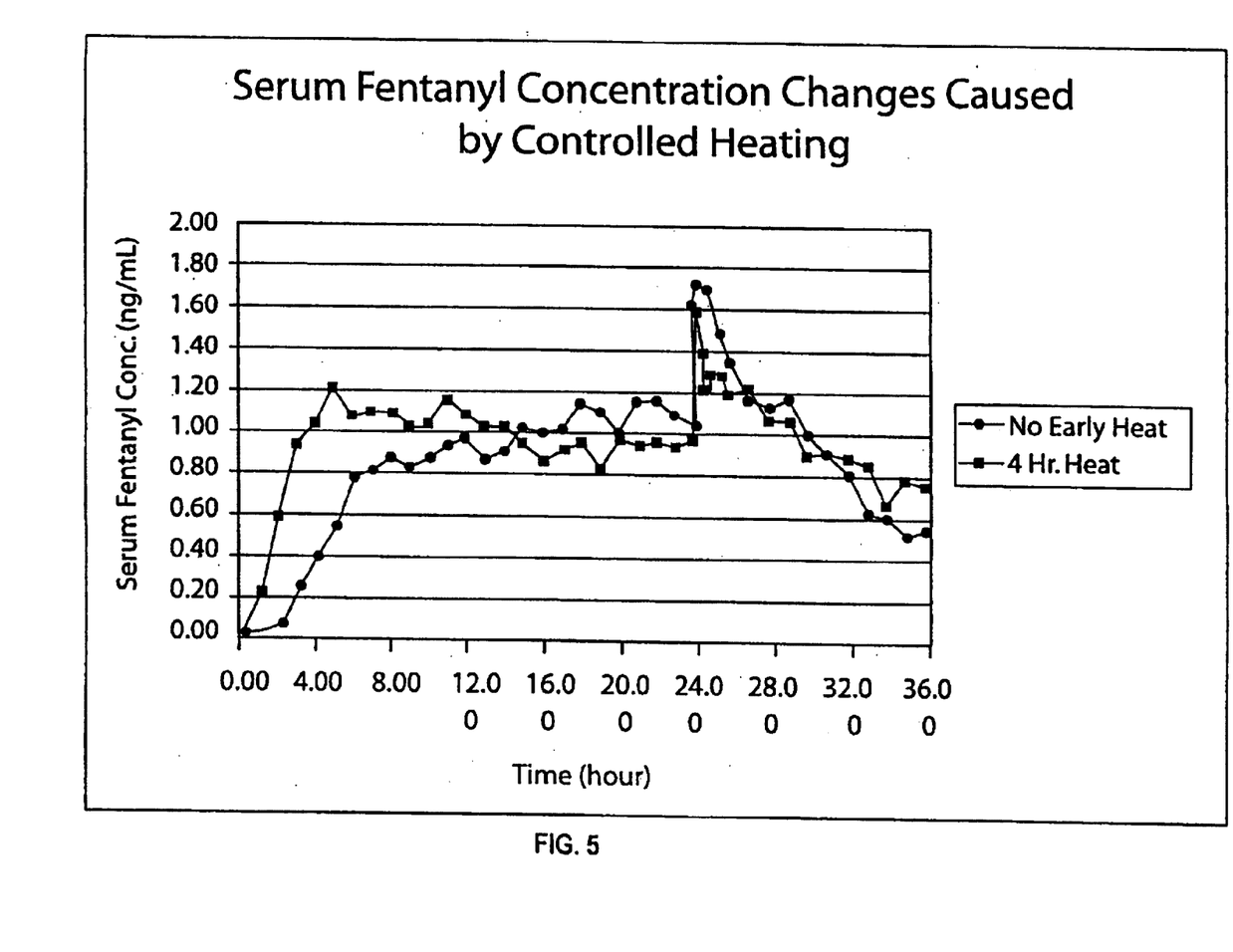
FIG. 5 shows a graph of serum fentanyl concentration changes caused by heating.

The device is similar to that of Example 3, except that the heating component has several independent sub-heating elements, as shown in FIGS. 3 and 4, each covering a fraction of the area (sub-area) of the drug patch. The drug patch is a transdermal fentanyl delivery patch. The control component also has the ability to activate one of more of the sub-heating elements at a time and thereby selectively heating one or more sub-areas. For example, the heating component has four sub-heating elements. The control component is designed so that when the delivery button (PCA button) is pushed for the first time, only the first sub-heating element is activated to heat about 25 percent of the fentanyl patch area (first sub-area) to a pre-determined temperature for a pre-determined time. Fentanyl in the depot in tissues under the heated area is then quickly released into the systemic circulation to treat breakthrough pain. When the PCA button is pushed for the second time, the control component activates the second sub-heating element, and so on. When the PCA button is pushed for the $5^{th}$ time, the first sub-heating element is activated again. By then, the depot under the first sub-heating element is re-filled. In this design, only a fraction of the total fentanyl depot is released into the systemic circulation at a time. This may minimize the overdose risk and allow each sub-depot time to re-fill after the depletion.

It is estimated that to effectively treat break through pain, a 15–20 percent increase in serum fentanyl concentration might be necessary and sufficient. Using the present invention, heating the entire patch and the corresponding depot areas and surrounding skin area yields a 70 percent increase in serum fentanyl concentration within 10 minutes. Therefore, it is possible and may be necessary that only a fraction of the fentanyl patch and corresponding depot site needs to be heated to provide sufficient additional fentanyl to treat breakthrough pain.

EXAMPLE 5

In this example, a device similar to that in Example 3 or 5 is used, but the device further comprises the feature that the heating component is an integral part of the drug patch. All the wires from the heating component (from each of the sub-heating elements, temperature sensor, etc.) are integrated into a connector capable of accommodating a matching connector with wires from the control component. When there is no need for bolus delivery, the patient wears the heating component-drug patch combination and enjoys the benefit of thermal insulation from the heating component. When there is a need to obtain a bolus dose, the patient hooks the heating component to the control component via the connectors and pushes the delivery button on the control component. After the bolus dose, the patient may disconnect the control component from the heating component.

EXAMPLE 6

In this example, the device is similar to that in Example 3 or 4, but further comprises the feature that the heating component is not an integral part of the drug patch but is connected to the control component by wires. The device comprises means for releasably affixing the heating component to the drug patch. For example, the heating component and the drug patch may have areas with matching loop and hook fasteners or a pouch attachment. In this way, the patient wears the drug patch alone when there is no need for bolus dose. When the need for bolus dose arises, the patient places the heating component onto the drug patch, the means for releasably affixing holds the heating component on the drug patch. The patient then pushes the delivery button on the control component to obtain the extra drug. After the bolus is delivered, the patient can remove the heating component from the drug patch without having to remove the drug patch.

Figure 1A:
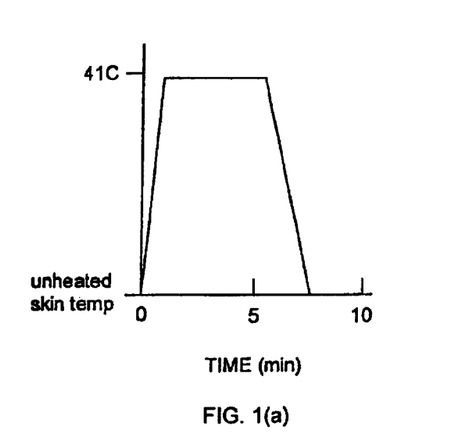
FIG. 1 shows some examples of the temperature vs. time profiles.
Figure 1B:
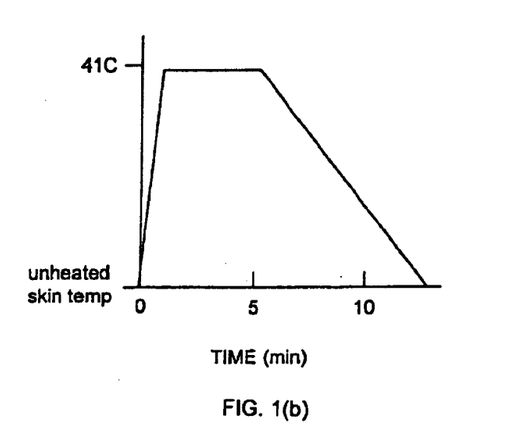
Figure 1C:
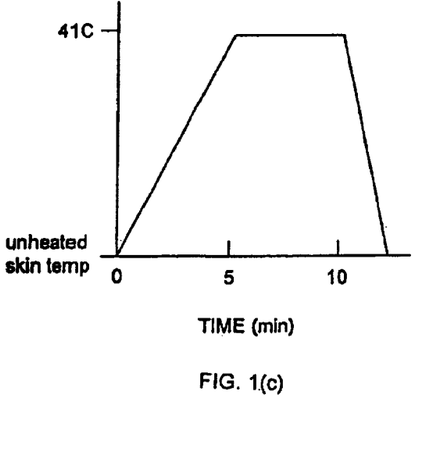
Figure 1D:
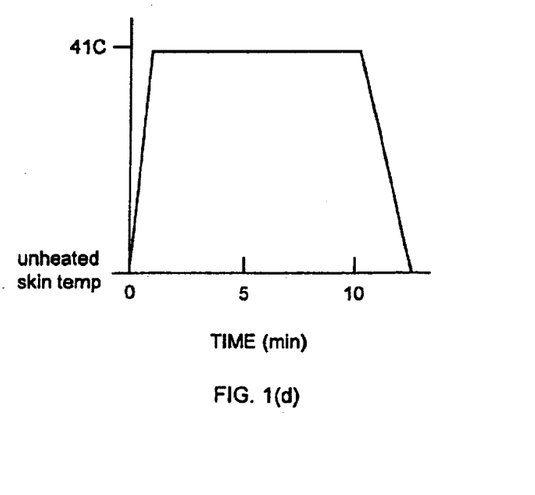
Figure 1E:
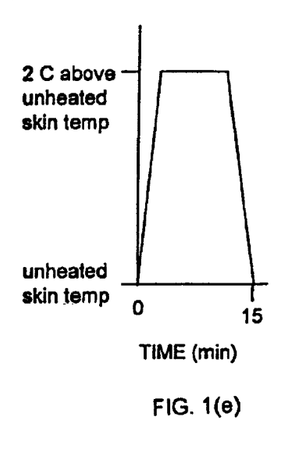
Figure 1F:
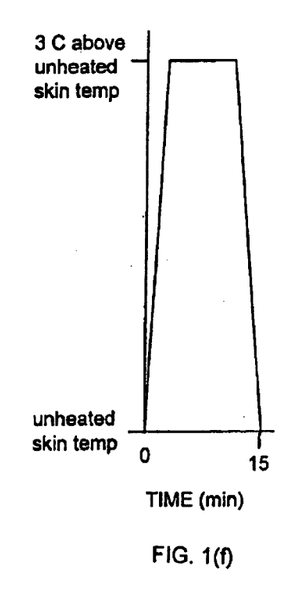
Figure 1G:
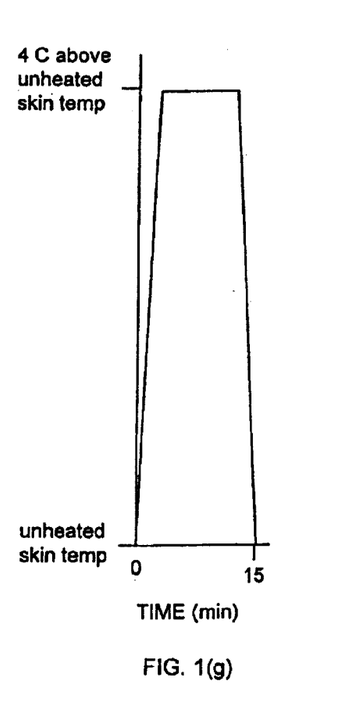
Figure 2:
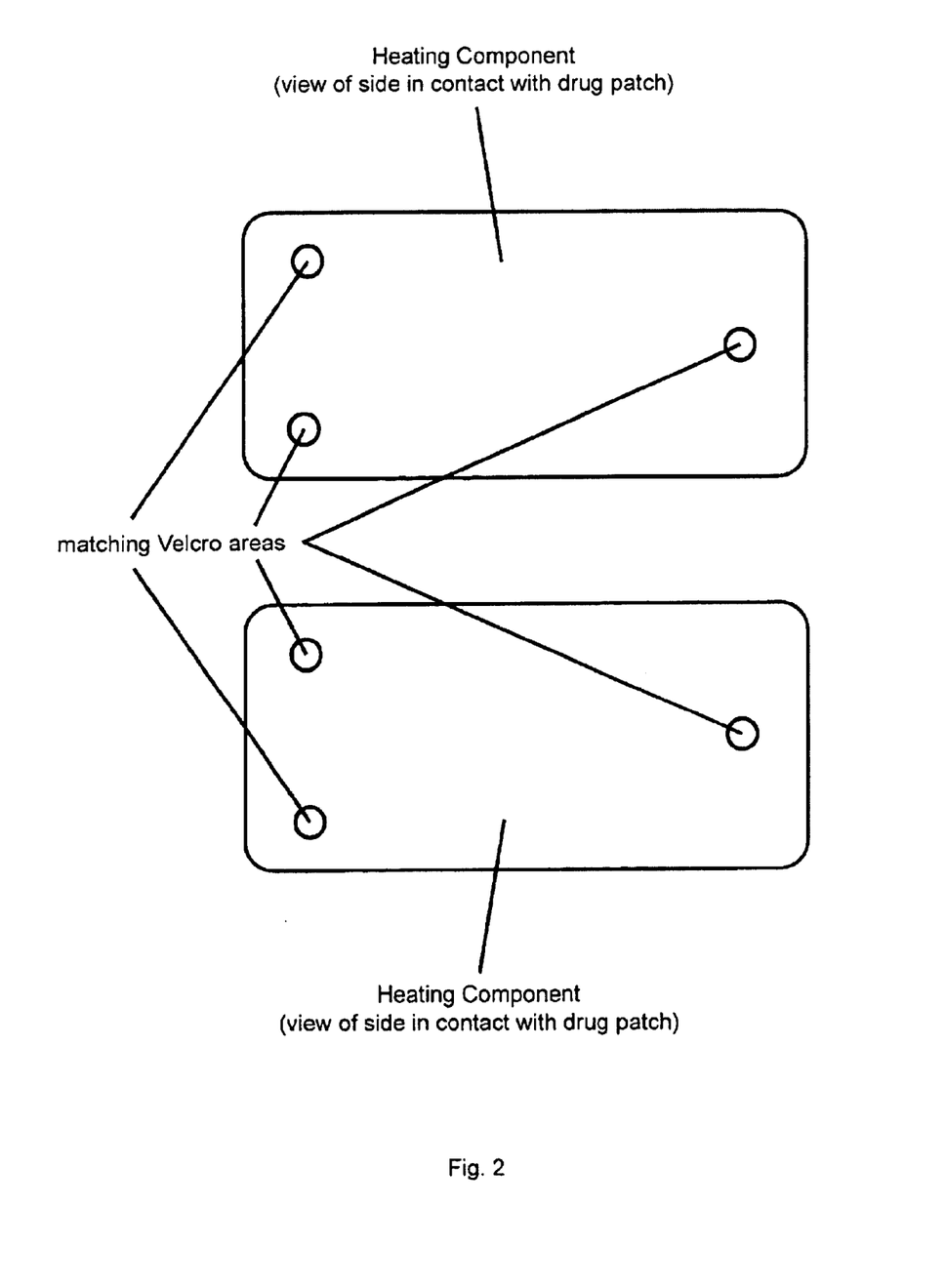
FIG. 2 is a heating component with means for affixing.

The means for affixing on the heating component and the drug patch can be designed so that there is only one way to affix the heating component onto the drug patch. By doing so, the sequential sub-area heating feature described in Example 3 may be used. Some of those means are shown in FIGS. 2 and 4.

Other means for affixing the heating component onto the drug patch include but are not limited to an adhesive with appropriate tackiness and reusability.

EXAMPLE 7

In this example, a heating component generates heat by chemical reaction such as by oxidation of iron powder. The heating component and the drug patch are designed so that there is only one way to affix the heating component on to the drug patch. The heating component, in the form of a patch, comes in several different designs, each with a heating area covering a different fraction of the drug patch area as shown in FIG. 3. The heating patches are in a dispenser that only allows the user to obtain the heating components according to a pre-arranged order. For example, the heating patches are stacked in a dispenser which only allow the user to take the top one before taking the next one. The pre-arranged order is such that the fractions of the drug patch area to be heated are in sequential order. In this way, the user activates the fractions of the depot area in a sequential order. The benefits of selectively heating a portion of the patch and depot site as discussed in Example 3 can thereby be obtained using an exothermic, oxidation heating element.

A heating component combination design similar to that shown in FIG. 4 may also be utilized here. The heating component (in the form of a disc) has four different designs, each with a heating area capable of covering a different fraction of the drug patch area. The heating disc has a wide side and a narrow wide, and the pouch on the back of the drug patch has three closed sides and one open side that can only allow the heating disc to slide in narrow side first. The heating discs are stored in the dispenser as discussed above. The sequential heating of the different fractions of the drug patch area can be achieved in the similar way as discussed above.

EXAMPLE 8

In this example, a heating device similar to the device in Example 3 with several sub-heating elements has a heating component that can be positioned on the fentanyl patch in only one orientation, so that the sub-skin areas under the patch can be heated in the desired order.

FIG. 4 describes a combination of a pouch on the back of the fentanyl patch and a heating disc that allows only one way to insert the disc into the pouch. The disc has a wider side and a narrower side. The pouch is closed on three sides but has an open mouth (dashed line). The wider side of the disc is wider than the mouth of the pouch, so that the disc can only be inserted into the pouch narrow-side first. If the patient removes the heating disc from the pouch after heating sub-skin area one, then places the heating disc into the pouch again to heat sub-skin area two to treat breakthrough episode number two, this configuration will guarantee that the heating is over sub-skin area two.

Similar methods/apparatus can also be used to guarantee the heating of right sub-skin area with chemical heating.

It may not be necessary to heat one-fourth of the entire area of the fentanyl patch in order to activate one-fourth of the drug depot in the tissues under the fentanyl patch. The reason is that heat under a sub-heating element can diffuse into areas surrounding the sub-heating element. Therefore, the area of the fentanyl patch covered by the sub-heating elements may be less than 100 percent. FIG. 4 reflects this idea. The desired area of a sub-heating element needs to be determined by experiments.

Although only transdermal fentanyl patch is discussed above with this pouch-heating disc combination, it should be pointed out that similar methods/apparatus may also be used with other transdermal drug patches.

Many drugs may be used in the systems of this invention. They include: analgesics, anesthetics, anti-arthritis drugs, anti-inflammatory drugs, anti-migraine drugs, cardiovascularly active drugs, smoke cessation drugs, hormones. Other potential drugs include, but are not limited to: androgen, estrogen, non-steroidal anti-inflammatory agents, anti-hypertensive agents, analgesic agents, anti-depressants, antibiotics, anti-cancer agents, local anesthetics, antiemetics, anti-infectants, contraceptives, anti-diabetic agents, steroids, anti-allergy agents, anti-migraine agents, agents for smoking cessation, and anti-obesity agents. Specific drugs can include without limitation nicotine, testosterone, estradiol, nitroglycerin, clonidine, dexamethasone, wintergreen oil, tetracaine, lidocaine, fentanyl, sufentanil, alfentanil and other potent mu-receptor agonists, progestrone, insulin, Vitamin A, Vitamin C, Vitamin E, prilocaine, bupivacaine, sumatriptan, scopolamine and dihydroergotamine.

EXAMPLE 9

The present invention may also comprise a non-invasive PCA fentanyl delivery system for treating post-surgical pain and the method of using it.

The system has three components: a transdermal fentanyl patch (preferably with means to accommodate a heating component, similar to that shown in FIG. 4), a control component and a heating component. The control component and the heating component are connected by conductive wires. The fentanyl patch is capable of delivering fentanyl through passive transdermal permeation. The heating unit and the control component are similar to that in Example 4, 5, 6 and 8. In addition, the device can be powered by both AC source or battery (batteries). The physician places the fentanyl patch on the skin of the patient at a time point during or after the surgery and selects the settings on the control component so that all-sub heating elements of the heating component heat the skin under them to about 40–42 C for 3.5 hours. With heating, serum fentanyl levels reach steady state in about 3–4 hours. Therefore, the time to initiate the fentanyl patch with heating is so chosen that fentanyl from the patch provides sufficient analgesia before the analgesia from the surgery runs out.

The control component has a PCA button and a set of dial switches (Bolus Dial), with each position on the Bolus Dial corresponding to a predetermined bolus dose. When the PCA button is pushed, the control component sends an electric current or voltage to particular sub-heating element(s) of the heating component. The magnitude and duration of the current or voltage, as well as which sub-heating element(s) to activate, are determined by the setting on the Bolus Dial. The control component sends no current or voltage to the heating component if the PCA button is pushed within the lockout time from last bolus dose. The lockout time is selected with another dial switch (Lockout Time Dial).

After the steady state blood fentanyl concentrations are reached, the physician may set the control component such that the patient can push the delivery button (a PCA button) to obtain a bolus dose when he/she feels the need to obtain more analgesic than the baseline delivery provided by the passive permeation of the patch. This phase of operation is referred as PCA mode hereafter. The control component allows the physician to select the proper bolus dose and proper lockout time.

The control component may have several possible embodiments for relating the settings on the Bolus Dial to different predetermined bolus doses. In one embodiment, each position on the Bolus Dial may correspond to a number of sub-heating elements to be activated. The heating component may have twenty sub-heating elements, and heating one of them to a predetermined temperature for a predetermined duration delivers one unit of the drug in the depot into the systemic circulation. Therefore, if the switch position of the Bolus Dial is at "1 unit" when the PCA button is pushed, one sub-heating element is supplied with pre-selected electric current or voltage for a predetermined duration. If the switch position is at "2 unit" when the PCA button is pushed, two heating elements are supplied with the current or voltage, and so on. The sub-heating elements to be activated are in a pre-determined sequential order if the PCA button is pushed multiple times (see Examples 4 and 8 for details and rationale).

In another embodiment, each position on the Bolus Dial corresponds to a different heating time. For example, the "1 unit" position heats 5 sub-heating elements for 1 minute, and the "3 unit" position heats 5 sub-heating elements for 3 minutes, and so on. However, the amount of bolus may not be linearly proportional to the duration of heating because more drug might be released from the depot per unit time of heating at the beginning of the heating when there is more drug in the depot. Therefore, a 3 unit bolus may require three more times the heating time than a 1 unit bolus. The actual heating duration for each bolus dose needs to be determined by experiments.

In another embodiment, combinations of the heating described above is produced.

The control unit may also be programmed such that it is automatically set into the PCA mode after the initial 3–4 hour heating.

Since each patient may need different baseline fentanyl delivery rates in the days after the surgery, the control unit may also have the mechanism to selectively heating a number of the sub-heating elements continuously throughout part or all of those post-surgical days. This mechanism can be in the form of another set of dial switches on the control unit (Baseline Rate Dial), with each position on the Baseline Rate Dial corresponds to continuously heating a selected number of sub-heating elements. For example, heating the skin to about 42 C may increase transdermal fentanyl delivery rates by a factor of about 4. A patient may receive satisfactory analgesia to control his post-surgical pain by the system without heating (after the initial heating to shorten the onset time). Another patient may need 60% more fentanyl to control the post-surgical pain after the initial heating. For the latter patient, the physician can select a position on the Baseline Rate Dial that causes 4 of the 20 sub-heating elements to continuously heat. Thus, the 4 elements (20% of all the elements) generates 4×20%=80% of drug input rate of an unheated patch, and the rest of the drug patch area also delivers 80% of the rate of an unheated patch. The result is that the patient gets 160% of the delivery rate of an unheated patch. The physician may also change the setting on the Baseline Rate Dial to change the number of sub-heating elements that continuously heat if the initial setting is too high or too low, or the patient's need changes. Therefore, this design allows the physician to precisely control the baseline drug delivery rates for each patient and make adjustments when necessary.

The above apparatus and method have several important advantages over the state of the art. Current passive transdermal fentanyl patches, such as Duragesic patches, are not suitable for post-operative pain control for several reasons, including long onset time (12–18 hours) and the lack of the ability to adjust fentanyl delivery rates either by the physician or the patient. They also don't have important features such as PCA dosing and lockout time. The above apparatus will significantly shorten the onset time, so that therapeutic levels of blood fentanyl can be established before the analgesia from the surgery runs out. The system lets the physician to select a proper PCA bolus dose for a particular patient, and allows the patient to obtain PCA doses by pushing the PCA button. The apparatus delivers fentanyl at a baseline rate and lets the physician make adjustments to the baseline delivery rate in a timely manner for each patient and to accommodate changing needs. This system has most of the important features of a modern PCA pump (baseline delivery, adjustable baseline delivery rates, adjustable bolus doses, lockout times), but also has the added advantage of being non-invasive.

It should be pointed out that the above system is not limited to using fentanyl as the analgesic. Any drug that can be delivered transdermally to provide sufficient analgesia may be used in the above system. These drugs include sufentanil, alfentanil, and other potent mu-receptor agonists.

EXAMPLE 10

The methods and apparatus are similar to that described in Example 3 through 8, except that the drug patch is a transdermal nicotine patch for smoke cessation. When the user has increased desire to smoke, he can release extra nicotine from the sub-patch depot using the apparatus.

EXAMPLE 11

A controlled release formulation comprising fentanyl and a controlled release hydrogel is injected into the sub-skin tissues of a patient to control post-surgical pain. The controlled release formulation is within 0.5 cm from the skin surface, so that heating of the skin can increase the temperature at the formulation. The fentanyl release rate is increased by heating because the heating increases blood circulation surrounding the formulation and/or increases the erosion speed of the formulation. This controlled release system provides sufficient fentanyl delivery rates to treat baseline pain of an average patient. If a particular patient needs more analgesic to control his pain, the physician may place the heating component of a device similar to that in Example 9 (control component and heating element, but no transdermal patch) onto the patient's skin under which the formulation resides and activates the right number of sub-heating elements to increase the delivery rates by the right percentage.

EXAMPLE 12

Similar to that in Example 11, except that in this case the controlled release formulation is used to treat cancer pain and the drug is sufentanil. The controlled release formulation is designed to deliver sufentanil at sufficient rates to treat baseline cancer pain for at least several months. When the patient needs extra sufentanil to treat breakthrough cancer pain, he/she uses the apparatus similar to that in Example 9 and 11 to obtain the bolus dose.

The present invention may be embodied in other specific forms without departing from its spirit or essential characteristics. The described embodiments and those disclosed in the attached appendix (if any) are to be considered in all respects only as illustrative and not restrictive. The scope of the invention is, therefore, indicated by the appended claims, rather than by the foregoing description. All changes which come within the meaning and range of equivalency of the claims are to be embraced within their scope.

What is claimed is:

1. A system for rapidly delivering a drug to a patient comprising:
   a drug in a drug depot site, wherein said drug depot site comprises at least one of skin and sub-skin tissues;
   a heating component to generate heat for heating the drug depot site; and
   a control component capable of controlling the magnitude and duration of heat generated by the heating component to achieve selective, precise, on-demand delivery of said drug from said drug depot site.

2. The system of claim 1, wherein said drug is in controlled release formulation.

3. The system of claim 1, wherein the drug depot site is disposed within the skin tissues.

4. The system of claim 1, wherein the drug depot site is disposed within the sub-skin tissues.

5. The system of claim 1, wherein the drug is injected into the skin.

6. The system of claim 1, wherein the drug is implanted into the skin.

7. The system of claim 1, wherein the drug depot site comprises an extra bolus of drug delivered into the patient's body.

8. The system of claim 1, wherein the drug is absorbed transdermally into the skin.

9. The system of claim 1, wherein the heating component is capable of generating heat when supplied with electric current.

10. The system of claim 9, wherein the control component receives a temperature signal from a temperature sensor proximate to the skin.

11. The system of claim 10, wherein the control component adjusts the electric current to the heating component according to the temperature sensor.

12. The system of claim 9, wherein the control component has settings that correspond to pre-determined electric power and heating time combinations.

13. The system of claim 9, wherein the control component also has mechanism to lockout a length of time in which the device generates no heat during drug administration.

14. The system of claim 9, wherein the control component is a mechanism that allows the patient to trigger delivery of a pre-determined amount of bolus drug from the depot site.

15. The system of claim 9, wherein the control component is activated using a button.

16. The system of claim 9, wherein the control component is pre-programmed to send an electric current with predetermined magnitude through a wire to the heating component for a pre-determined length of time.

17. The system of claim 16, wherein the magnitude and the pre-determined length of time of the current produce a temperature increase at the skin for a pre-determined length of time that releases a pre-determined amount of the drug from the depot site.

18. The system of claim 16, wherein the magnitude of the current is designed to produce several heating temperature vs. time profiles to accommodate different needs.

19. The system of claim 1, wherein the control component safely and effectively delivers the bolus drug from sub-skin tissues by heating.

20. The system of claim 1, wherein the heating component is preferably an electric heating component.

21. The system of claim 1, further comprising a microprocessor in conjunction with the electric heating component.

22. The system of claim 1, wherein the electric heating component and control component are connected by electric wires.

23. The system of claim 1, wherein the heating component has a temperature sensor that measures the temperature at the drug patch and transmits the measure temperature to the control component to regulate the heating temperature.

24. The system of claim 1, wherein the heating component has a layer of thermal insulating material on the side not in contact with the drug patch for minimizing heat loss.

25. The system of claim 1, wherein the control component has a plurality of settings for controlling heat, each setting delivering a different amount of heating energy to the skin site.

26. The system of claim 12, wherein the electric power associated with each said setting is pre-determined.

27. The system of claim 1, wherein the drug in the drug depot site is delivered into the skin from a transdermal drug patch.

28. The system of claim 27, wherein the drug patch is an analgesic drug patch.

29. The system of claim 27, wherein said patch is applied on the skin of the patient for predetermined period to create a depot site.

30. The system of claim 27, wherein further comprising means for releasably affixing the heating component to the drug patch.

31. The system of claim 30, wherein the heating component and the drug patch have areas with corresponding loop and hook fasteners.

32. The system of claim 30, wherein means for affixing the heating component to the drug patch can only be affixed in a prescribed orientation.

33. The system of claim 30, wherein means for affixing the heating component comprises to an adhesive with appropriate tackiness and reusability.

34. The system of claim 1, wherein said heating component is an exothermic oxidation heating patch.

35. The system of claim 34, wherein the exothermic oxidation heating patch comprises a heating area covers a portion of the drug patch area.

36. The system of claim 34, wherein the heating component is a disposable heating component.

37. The system of claim 1, wherein the drug is selected from the group of: analgesics, anesthetics, anti-arthritis drugs, anti-inflammatory drugs, anti-migraine drugs, cardiovascularly active drugs, smoke cessation drugs, hormones, androgen, estrogen, non-steroidal anti-inflammatory agents, anti-hypertensive agents, analgesic agents, anti-depressants, antibiotics, anti-cancer agents, local anesthetics, antiemetics, anti-infectants, contraceptives, anti-diabetic agents, steroids, anti-allergy agents, anti-migraine agents, agents for smoking cessation, anti-obesity agents, nicotine, testosterone, estradiol, nitroglycerin, clonidine, dexamethasone, wintergreen oil, tetracaine, lidocaine, fentanyl, sufentanil, alfentanil and other potent mu-receptor agonists, progestrone, insulin, Vitamin A, Vitamin C, Vitamin E, prilocaine, bupivacaine, sumatriptan, scopolamine and dihydroergotamine.

* * * * *